(12) United States Patent
Cha et al.

(10) Patent No.: US 7,341,759 B2
(45) Date of Patent: Mar. 11, 2008

(54) ELECTRICALLY CONDUCTIVE POLYMER, SENSOR USING THE SAME, AND METHOD FOR DETECTING TARGET MOLECULE USING THE SENSOR

(75) Inventors: Jun-hoe Cha, Kyungki-do (KR); Young Choi, Kyungki-do (KR); Jung-im Han, Seoul (KR); Geun-bae Lim, Kyungki-do (KR)

(73) Assignee: Samsung Electronics Co., Ltd. (KR)

( * ) Notice: Subject to any disclaimer, the term of this patent is extended or adjusted under 35 U.S.C. 154(b) by 451 days.

(21) Appl. No.: 11/134,984

(22) Filed: May 23, 2005

(65) Prior Publication Data
US 2005/0208579 A1 Sep. 22, 2005

Related U.S. Application Data

(62) Division of application No. 10/383,809, filed on Mar. 6, 2003, now Pat. No. 6,987,164.

(30) Foreign Application Priority Data

Mar. 9, 2002 (KR) ................... 2002-12729
Feb. 7, 2003 (KR) ................... 2003-7757

(51) Int. Cl.
*B05D 5/12* (2006.01)
*C08G 15/00* (2006.01)
(52) U.S. Cl. .............. 427/59; 427/58; 528/373; 528/375; 528/310
(58) Field of Classification Search ............ 427/58, 427/59; 528/373, 375, 310
See application file for complete search history.

(56) References Cited

U.S. PATENT DOCUMENTS 6,201,086 B1 3/2001 Garnier 6,770,190 B1 8/2004 Milanovski et al. ..... 205/777.5

FOREIGN PATENT DOCUMENTS

WO WO 00/31750 6/2000

OTHER PUBLICATIONS

F.M. Matschinsky and M.A. Magnuson, "Molecular Pathogenesis of MODYs", Karger, 2000, vol. 15, pp. 16-32.
Bauerle P. and Emge A., Adv. Materi., 3:324 (1998).
"Reactive groups on polymer coated electrodes, 8 Novel conducting polymer interfaces produced by electrochemical copolymerization of functionalized thiophene activated esters with 3-methylthiophene";Authors: Guangtao Li, Gerhard Kobmehl, Hans-Peter Welzel, Gunnar Engelmann, Wolf-Dietrich Hunnius, Waldfried Plieth and Hesun Zhu; XP-000787914; WILEY-VCH Verlag GmbH, D-69451 Weinheim; Macromol. Chem. Phys., vol. 199, No. 10; 1998; pp. 2255-2266.

(Continued)

*Primary Examiner*—Duc Truong
(74) *Attorney, Agent, or Firm*—Cantor Colburn LLP

(57) ABSTRACT

A novel electrically conductive polymer, a sensor using the electrically conductive polymer, and a method for detecting a target molecule that hybridizes to a probe, using the sensor, are provided. The electrically conductive polymer has the following formula:

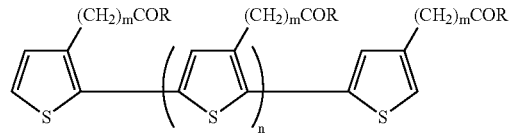

where m is 1, 2, or 3; R is a hydroxysuccinimidyl group, a hydroxyphthalimidyl group, or a pentafluorophenolyl group; and n is zero or an integer.

8 Claims, 11 Drawing Sheets

OTHER PUBLICATIONS

"Amperometric Biosensors Produced b Immobilization of Redox Enzymes at Polythiophene-Modified Electrode Surfaces"; Authors: Markus Hiller, Christine Kranz, Johanna Huber, Peter Bauerle and Wolfgang Schuhmann; XP-000558248; WILEY-VCH Verlag GmbH, D-69469 Weinheim, Advanced Materials, vol. 8, No. 3; pp. 219-222.

European Search Report; Application No. 03004957.1-1218; Date of Completion: Mar. 18, 2004.

Li et al; Reactive groups on polymer coated electrodes; 1988; Huethig & Wept Verlag; Chem Abstract 129:316666.

Office Action from The Patent Office of the People's Republic of China for Application No. 03130785X.

Office Action issued by the Korean Patent Office for Application No. 10-2003-0007757 on Apr. 29, 2005.

```
SEQUENCE LISTING

<160> NUMBER OF SEQ ID NOS: 4

<210> SEQ ID NO 1
<211> LENGTH: 15
<212> TYPE: DNA
<213> ORGANISM: Artificial
<220> FEATURE:
<223> OTHER INFORMATION: probe DNA

<400> SEQUENCE: 1
gttcttctca tcatc                                                    15

<210> SEQ ID NO 2
<211> LENGTH: 15
<212> TYPE: DNA
<213> ORGANISM: Artificial
<220> FEATURE:
<223> OTHER INFORMATION: a target DNA which is completely complementary
      to the probe DNA(SEQ ID NO. 1)

<400> SEQUENCE: 2
gatgatgaga agaac                                                    15

<210> SEQ ID NO 3
<211> LENGTH: 15
<212> TYPE: DNA
<213> ORGANISM: Artificial
<220> FEATURE:
<223> OTHER INFORMATION: a target DNA which is complementary to the
      prove DNA (SEQ ID NO. 1) except 1 base

<400> SEQUENCE: 3
gatgatggga agaac                                                    15

<210> SEQ ID NO 4
<211> LENGTH: 15
<212> TYPE: DNA
<213> ORGANISM: Artificial
<220> FEATURE:
<223> OTHER INFORMATION: a target DNA which is completely complementary
      to the prove DNA (SEQ ID NO. 1) except 1 base

<400> SEQUENCE: 4
gatgatgcga agaac                                                    15
```

ELECTRICALLY CONDUCTIVE POLYMER, SENSOR USING THE SAME, AND METHOD FOR DETECTING TARGET MOLECULE USING THE SENSOR

CROSS REFERENCE TO RELATED APPLICATIONS

This application is a divisional application of U.S. patent application Ser. No. 10/383,809, filed Mar. 6, 2003 now U.S. Pat. No. 6,987,164, in the U.S. Patent and Trademark Office, which claimed the benefit of the filing date of Mar. 9, 2002 to Korean Patent Application No. 2002-12729 and the filing date of Feb. 7, 2003 to Korean Patent Application No. 2003-7757, the disclosure of which is incorporated herein in its entirety by reference.

BACKGROUND OF THE INVENTION

1. Field of the Invention

The present invention relates to a novel electrically conductive polymer, a sensor having an electrode coated with the electrically conductive polymer, and a method for detecting a target molecule using the sensor.

2. Description of the Related Art

There have been many studies on the development of biomolecule detecting sensors based on the electrochemical principles. One advantage of using the electrochemical principles lies in that sensors can be miniaturized. Accordingly, there have been great advances in research on electrochemical sensors, such as ionic sensors, gas sensors, biosensors, etc. In the fields of genomics and proteomics, it is very important to monitor information on the hybridization of DNA, among other biological molecules, and to monitor conformational changes of proteins. To this end, there have been developed sensors using organic materials, such as intercalators having electrochemical activities, and using electrically conductive polymers. In particular, intercalator-based sensors are ready to be released on the market as a result of extensive research thereon.

In conductive polymer sensors, only a few representative monomers capable of being polymerized on electrodes are available, and it is difficult to control the physical properties of polymers. As a result, research thereon has been relatively slow. Representative materials for conductive polymer sensors include pyrroles, thiophenes, anilines, and the like. However, because of a limitation that anilines are effective only in acidic conditions, pyrroles and thiophenes have been the main focus of research.

However, pyrroles cannot be used for a long duration due to their small redox potential (U.S. Pat. No. 6,201,086). Thiophenes have a higher redox potential but are more hydrophobic than pyrroles, so they are unsuitable for biomolecule dispersion systems in water (Bauerle P. and Emge A., Adv. Materi., 3:324 (1998)).

SUMMARY OF THE INVENTION

The present invention provides a novel electrically conductive polymer.

The present invention also provides novel monomer compounds capable of being polymerized into the electrically conductive polymer.

The present invention also provides an electrode coated with the electrically conductive polymer.

The present invention also provides a sensor having an electrode coated with the electrically conductive polymer.

The present invention also provides a method for detecting a target molecule using the sensor.

According to an aspect of the present invention, there is provided an electrically conductive polymer having formula (I) below:

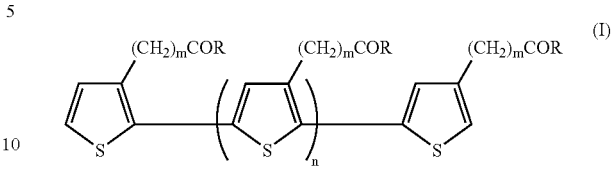

where m is 1, 2, or 3; R is a hydroxysuccinimidyl group, a hydroxyphthalimidyl group, or a pentafluorophenolyl group; and n is zero or an integer.

An electrically conductive polymer according to the present invention may have formula (II) below:

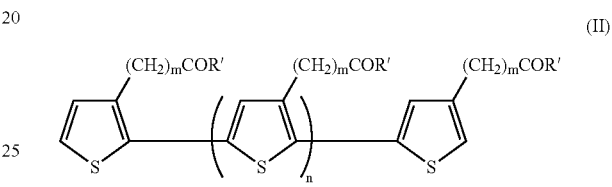

where m is 1, 2, or 3; R' is a hydroxysuccinimidyl group, a hydroxyphthalimidyl group, a pentafluorophenolyl group, or a probe group, wherein at least one R' is a probe group; and n is zero or an integer.

According to another aspect of the present invention, there is provided a monomer used for the synthesis of any electrically conductive polymer according to the present invention described above, being N-hydroxyphthalimidyl 3-thiophenlyl acetate or 3-pentafluorophenolyl 3-thiophenylyl acetate.

According to another aspect of the present invention, there is provided a method for detecting a target molecule, comprising: (a) providing the electrically conductive polymer having formula (I) above on a substrate through electrical polymerization; (b) immobilizing a probe to the surface of the electrically conductive polymer; (c) contacting a sample containing a target molecule, which is capable of specifically reacting with the probe, to hybridize with the probe; and (d) detecting the target molecule by measuring a voltage or current variation in the electrically conductive polymer.

Another method for detecting a target molecule according to the present invention comprises: (a) providing the electrically conductive polymer of formula (II) above on a substrate through electrical polymerization; (b) contacting a sample containing a target molecule, which is capable of specifically reacting with the probe, to hybridize with the probe bonded to the electrically conductive polymer; and (c) detecting the target molecule by measuring a voltage or current variation in the electrically conductive polymer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

An electrically conductive polymer according to the present invention has formula (I) below:

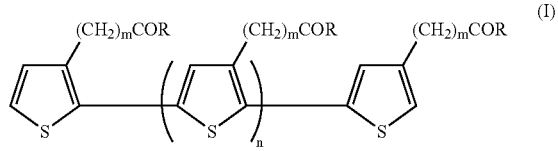

where m is 1, 2, or 3; R is a hydroxysuccinimidyl, hydroxyphthalimidyl, or pentafluorophenolyl group; and n is zero or an integer.

Another electrically conductive polymer according to the present invention has formula (II) below:

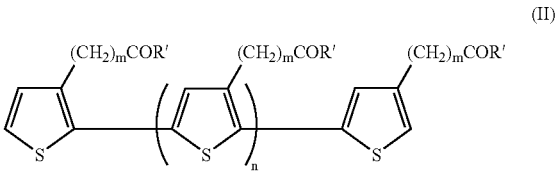

where m is 1, 2, or 3; R' is a hydroxysuccinimidyl group, a hydroxyphthalimidyl group, a pentafluorophenolyl group, or a probe group, wherein at least one R' is a probe group; and n is zero or an integer.

The term "probe" used throughout the specification means a molecule capable of specifically binding to a target material. Examples of such a probe includes a nucleic acid and a protein, in which a deoxyribonucleic acid (DNA), a ribonucleic acid (RNA), a peptide nucleic acid (PNA), an antibody, an antigen, an enzyme, a cofactor, and a substrate are preferred as the probe.

Electrically conductive polymers according to the present invention may be synthesized from monomers through polymerization by cyclic voltammetry, chronopotentiometry, chronoamperometry, and the like. The electrically conductive polymers according to the present invention have a high redox potential.

The present invention provides monomers capable of forming, through polymerization, an electrically conductive polymer according to the present invention. Preferred examples of such monomers include N-hydroxyphthalimidyl 3-thiophenlyl acetate having formula (III) below and pentafluorophenolyl 3-thiophenyl acetate having formula (IV) below.

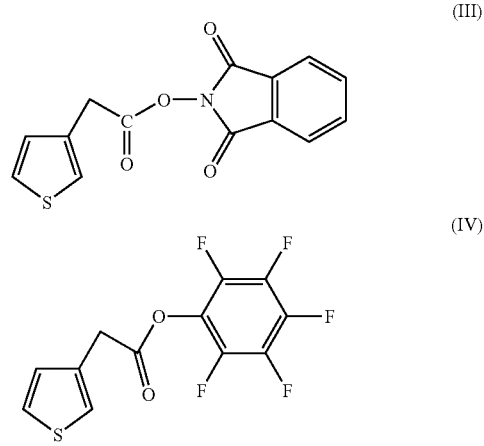

The present invention provides an electrode coated with an electrically conductive polymer according to the present invention. Any material commonly used in forming electrodes, for example, platinum, may be used for the electrode according to the present invention.

The present invention provides a sensor employing an electrode coated with an electrically conductive polymer according to the present invention. The sensor according to the present invention includes common sensor constituent elements except for an electrode coated with an electrically conductive polymer according to the present invention. The sensor according to the present invention may include a working electrode, a counter electrode, and a reference electrode, which are commonly used.

Figure 1:
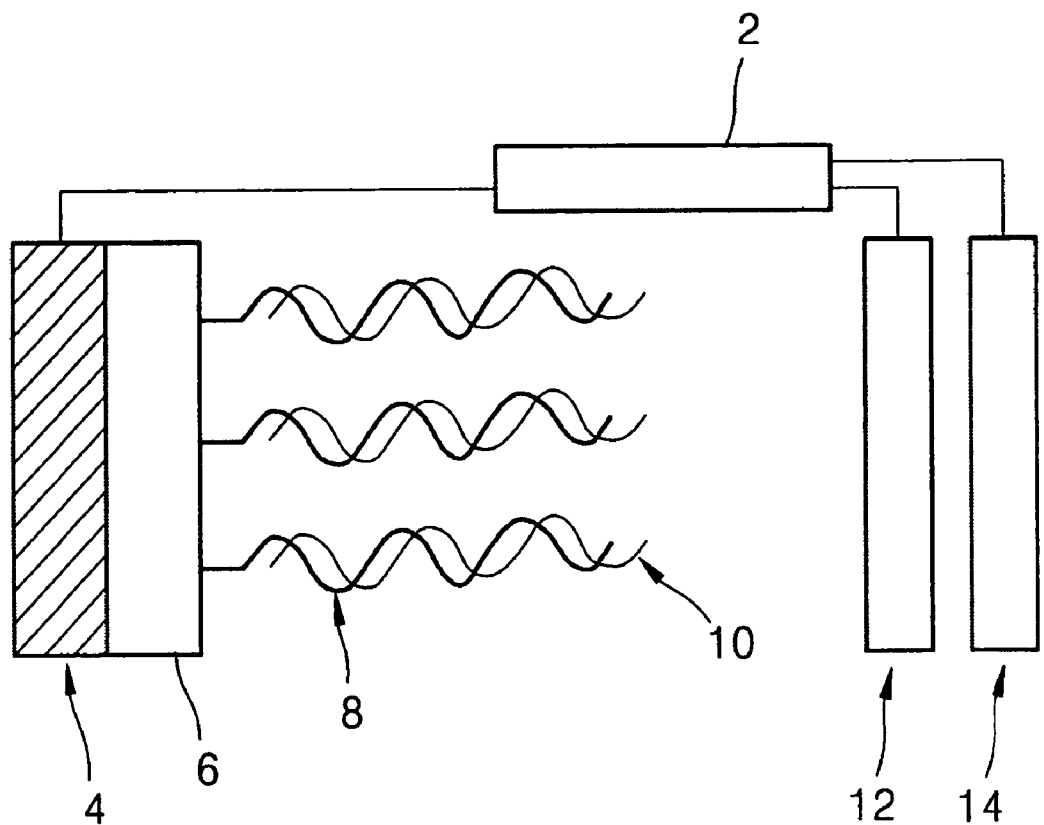
FIG. 1 illustrates an embodiment of a sensor employing an electrode coated with an electrically conductive polymer according to the present invention.

FIG. 1 illustrates an embodiment of a sensor employing an electrode coated with an electrically conductive polymer according to the present invention. Referring to FIG. 1, a sensor according to the present invention includes a working electrode 4 coated with an electrically conductive polymer 6 according to the present invention that is covalently bonded with a probe 8, a counter electrode 12, and a reference electrode 14, and a potentiostat 2 for measuring potential.

The working electrode 4 coated with the electrically conductive polymer 6 according to the present invention may be manufactured as follows. Initially, a monomer, a kind of thiophene compound having an amine group capable of binding to a probe, is synthesized. Thiophene monomers capable of being electrically polymerized are preferred. The synthesized monomer is subject to polymerization over a substrate and bound with a probe, for example, DNA, thereby resulting in an electrode according to the present invention that is coated with an electrically conductive polymer according to the present invention covalently bonded with a probe. Alternatively, after covalently bonding the probe 8 to a thiophene monomer, the thiophene monomer with the probe 8 may be subject to polymerization over a substrate, thereby resulting in an electrode according to the present invention that is coated with an electrically conductive polymer according to the present invention covalently bonded with a probe. The electrode manufactured through the above processes is used as the working electrode 4.

A target molecule 10 of interest in samples can be detected using the above sensor according to the present invention. When a sample containing the target molecule 10 is brought to contact the probe 8 that is immobilized on the working electrode 4 of the sensor, the target molecule 10 hybridizes to the probe 8, as illustrated in FIG. 1, a voltage or current variation from the hybridization reaction is read, so that the target molecule 10 in the sample can be identified.

Voltage or current variations occurring from hybridization are thought to follow, though not absolutely, the mechanism described below. The electrical current at a particular redox potential depends on the delocalization in the electrically conductive polymer on the substrate. The degree of delocalization in the electrically conductive polymer after a target molecule hybridizes to the probe that is covalently bonded to the electrically conductive polymer according to the present invention is smaller than before the hybridization. Accordingly, when a target metal hybridizes to a probe, the electrical current decreases. In other words, when a double stranded DNA is formed as a result of the hybridization of a DNA probe and a target DNA, the electrical current becomes small. Therefore, a target molecule in a sample can be detected by measuring a decrease in the amount of redox potential that occurs when the target molecule hybridizes to a probe or an increase when not.

Figure 2:
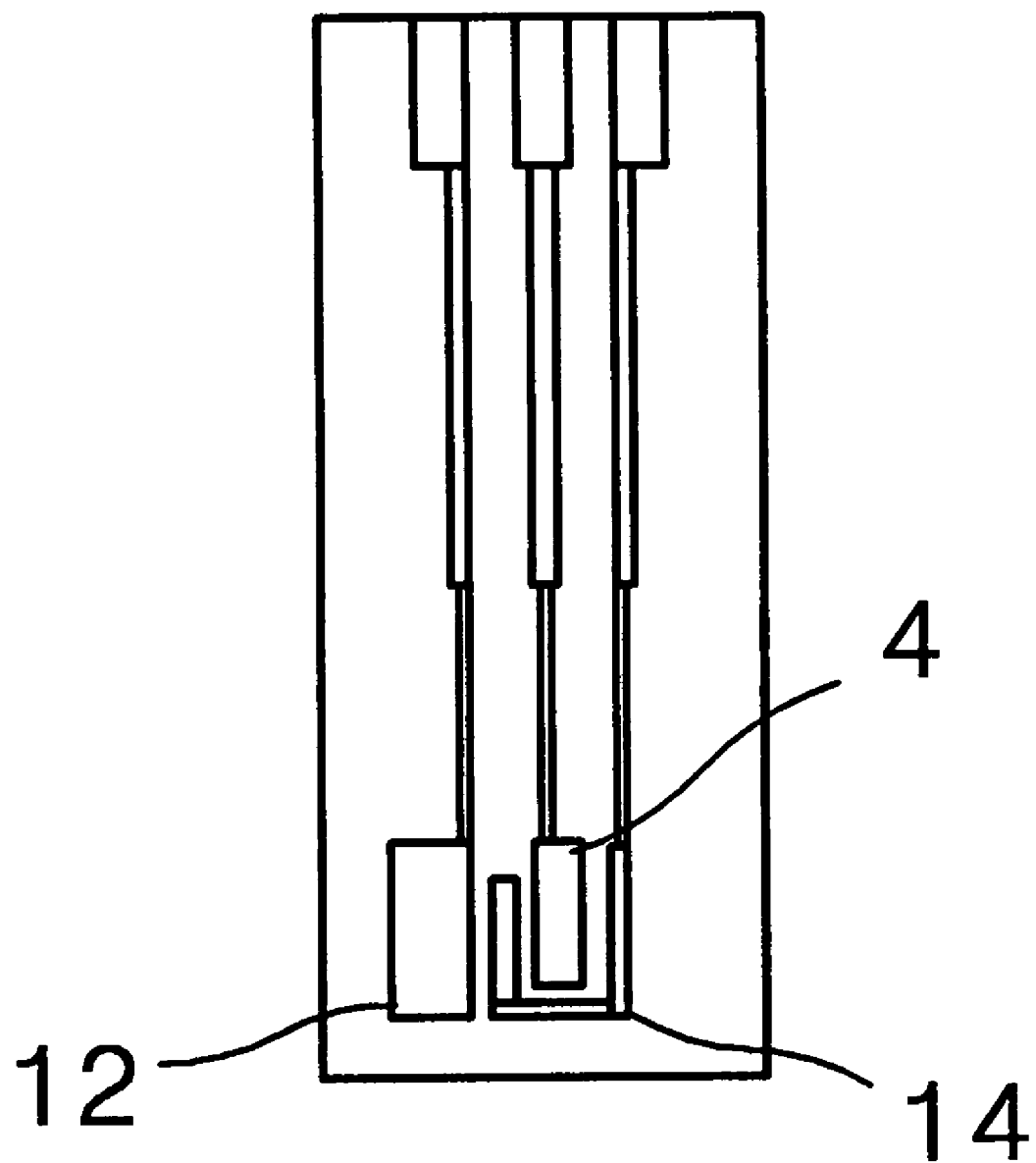
FIG. 2 shows another embodiment of a sensor using an electrically conductive polymer according to the present invention.

FIG. 2 shows another embodiment of a sensor using an electrically conductive polymer according to the present invention. The sensor of FIG. 2 includes a working electrode 4, a counter electrode 12, and a reference electrode 14. The working electrode 4 is coated with an electrically conductive polymer according to the present invention.

The present invention provides a method for detecting a target molecule, the method including:

(a) providing an electrically conductive polymer, a kind of polythiophene, on a substrate through electrical polymerization;

(b) immobilizing a probe to the surface of the electrically conductive polymer;

(c) contacting a sample containing a target molecule, which is capable of specifically reacting with the probe, to hybridize with the probe; and (d) detecting the target molecule by measuring a voltage or current variation in the electrically conductive polymer.

The present invention provides another method for detecting a target molecule, the method including:

(a) providing an electrically conductive polymer, a kind of polythiophene, bonded with a probe on a substrate through electrical polymerization;

(b) contacting a sample containing a target molecule, which is capable of specifically reacting with the probe, to hybridize with the probe bonded to the electrically conductive polymer; and (c) detecting the target molecule by measuring a voltage or current variation in the electrically conductive polymer.

It is preferable that the conductive substrate be a gold or platinum electrode. Examples of such a probe include, preferably, a DNA, an RNA, a PNA, an antibody, an antigen, an enzyme, a substrate, and a cofactor. Such a target molecule may include any material capable of specifically binding to the probe, preferably, a nucleic acid or a protein.

Hereinafter, the present invention will be described in greater detail with reference to the following examples. The following examples are for illustrative purposes and are not intended to limit the scope of the invention.

EXAMPLE 1

Synthesis of N-hydroxyphthalimidyl 3-thiophenlyl acetate

N-hydroxyphthalimidyl 3-thiophenlyl acetate as a monomer to be used in the synthesis of an electrically conductive polymer according to the present invention was synthesized as follows. One equivalent of 3-thiophenyl acetic acid and 1 equivalent of 3-hydroxyl phthalimide were reacted in chloroform at room temperature in the presence of N,N'-dicyclohexyl carbodiimide (DCC), as shown in a reaction scheme below. The reaction product was purified through recrystallization. The resulting purified compound was confirmed to be N-hydroxyphthalimidyl 3-thiophenlyl acetate having formula (III) above by NMR.

$^1$H NMR(CDCl$_3$): 7.87(m, C$_6$H$_4$, 4H), 7.31(m, C$_4$H$_3$SCH$_2$, 1H), 7.24(s, C$_4$H$_3$SCH$_2$, 1H), 7.11(m, C$_4$H$_3$SCH$_2$, 1H), 4.01(s, C$_4$H$_3$SCH$_2$, 2H).

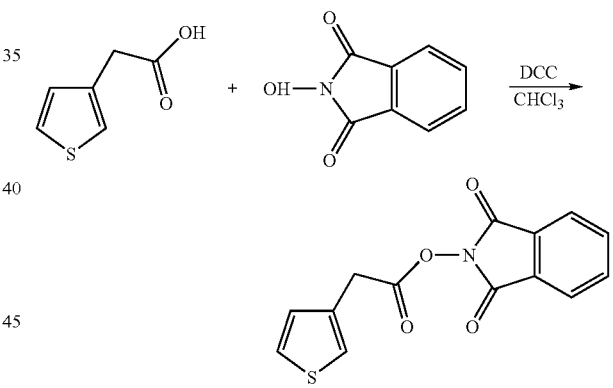

EXAMPLE 2

Synthesis of 3-pentafluorophenolyl 3-thiophenylyl Acetate 3-pentafluorophenolyl 3-thiophenylyl acetate as a monomer to be used in the synthesis of an electrically conductive polymer according to the present invention was synthesized as follows. One equivalent of 3-thiophenyl acetic acid and 1 equivalent of pentafluorophenol were reacted in chloroform at room temperature in the presence of DCC. The reaction product was purified through column chromatography on silica gels. The resulting purified compound was confirmed to be 3-pentafluorophenolyl 3-thiophenylyl acetate having formula (IV) above by NMR.

$^1$H NMR(CDCl$_3$): 7.82 (2H), 7.72 (2H), 7.28 (1H), 7.26 (1H), 7.07(1H), 4.0 (2H)

EXAMPLE 3

Figure 3:
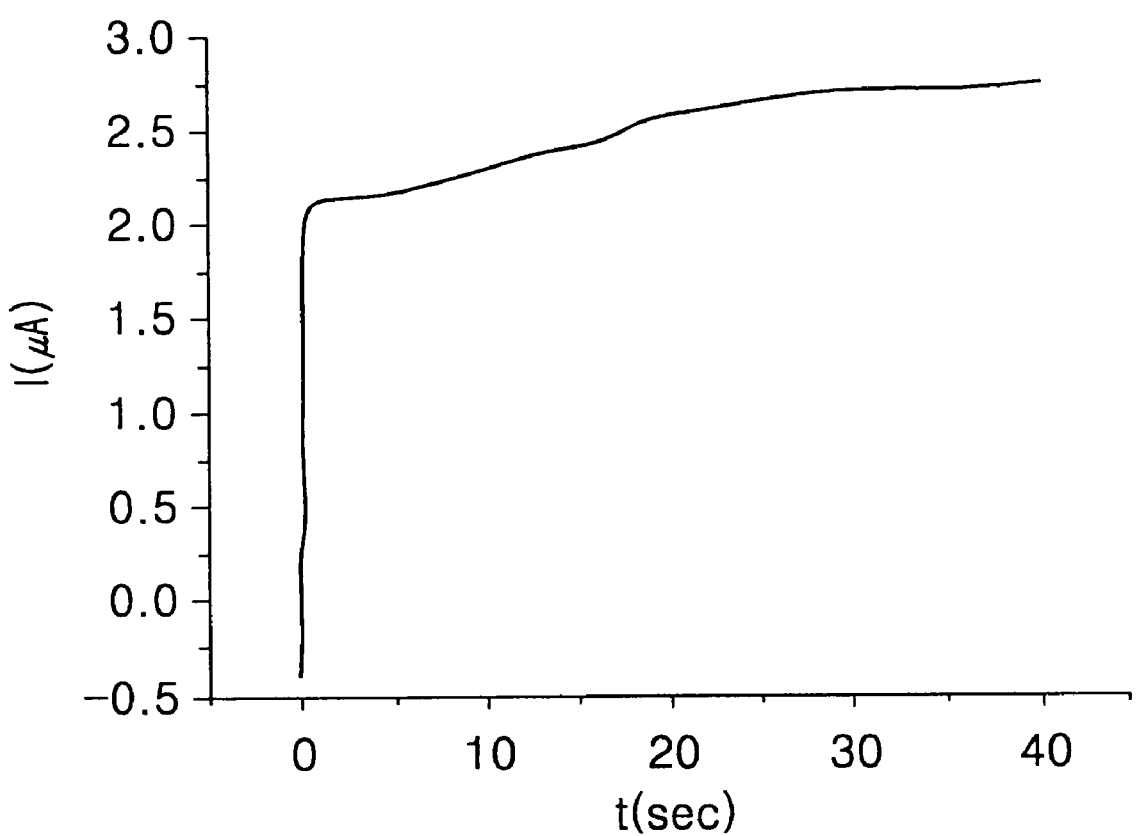
FIG. 3 is a graph illustrating an example of polymerization using chronopotentiometry for an electrically conductive polymer according to the present invention.

Polymerization Over an Electrode 0.1M of the N-hydroxyphthalimidyl 3-thiophenlyl acetate having formula (III) above synthesized in Example 1 was dissolved in a solution of 0.1M of tetrabutylamine hexafluorophosphate (TBAHFP) as a dopant in acetonitrile, and polymerization of the monomer was induced over a platinum electrode using chronopotentrometry, as illustrated in FIG. 3. In particular, a platinum electrode was placed on a 0.5-mm-thick glass substrate, and polymerization of the monomer was induced at a current of 0.4 mA for 40 seconds to uniformly form an electrically conductive polymer layer on the platinum electrode.

Figure 4:
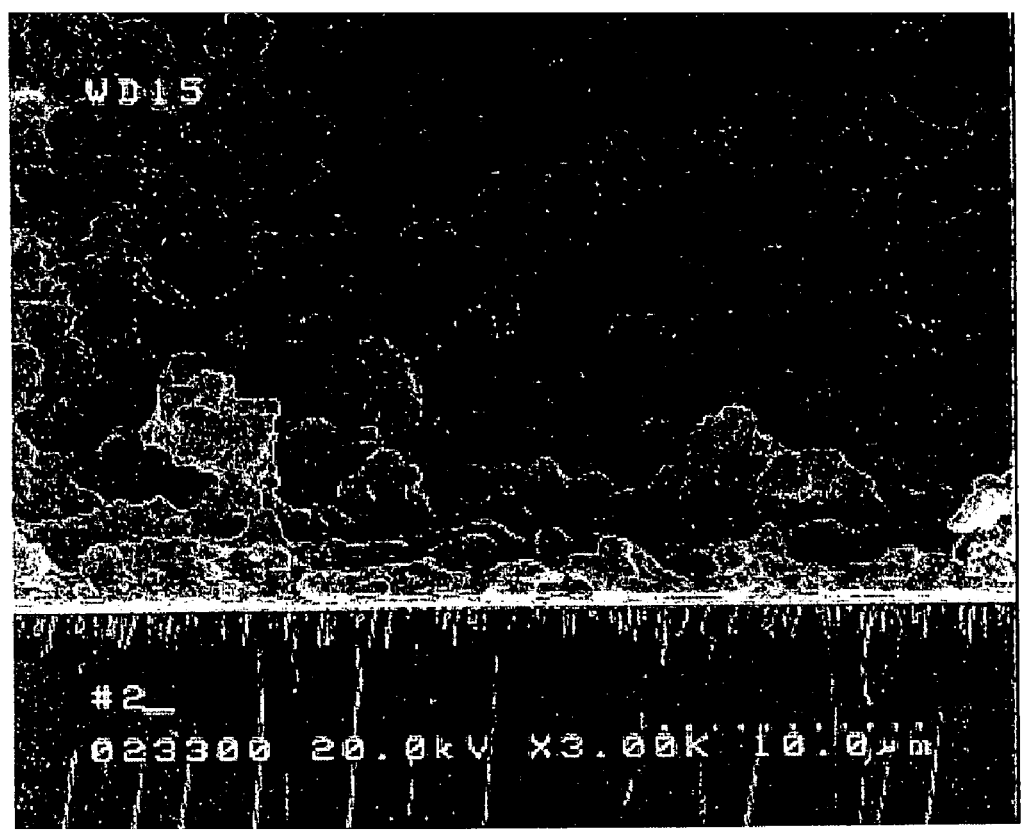
FIG. 4 is a scanning electron microscopic photograph of an electrically conductive polymer layer according to the present invention polymerized by chronopotentiometry.

This electrically conductive polymer layer of poly(N-hydroxyphthalimidyl 3-thiophenlyl acetate) was observed using a scanning electron microscope. The result is shown in FIG. 4.

Figure 5:
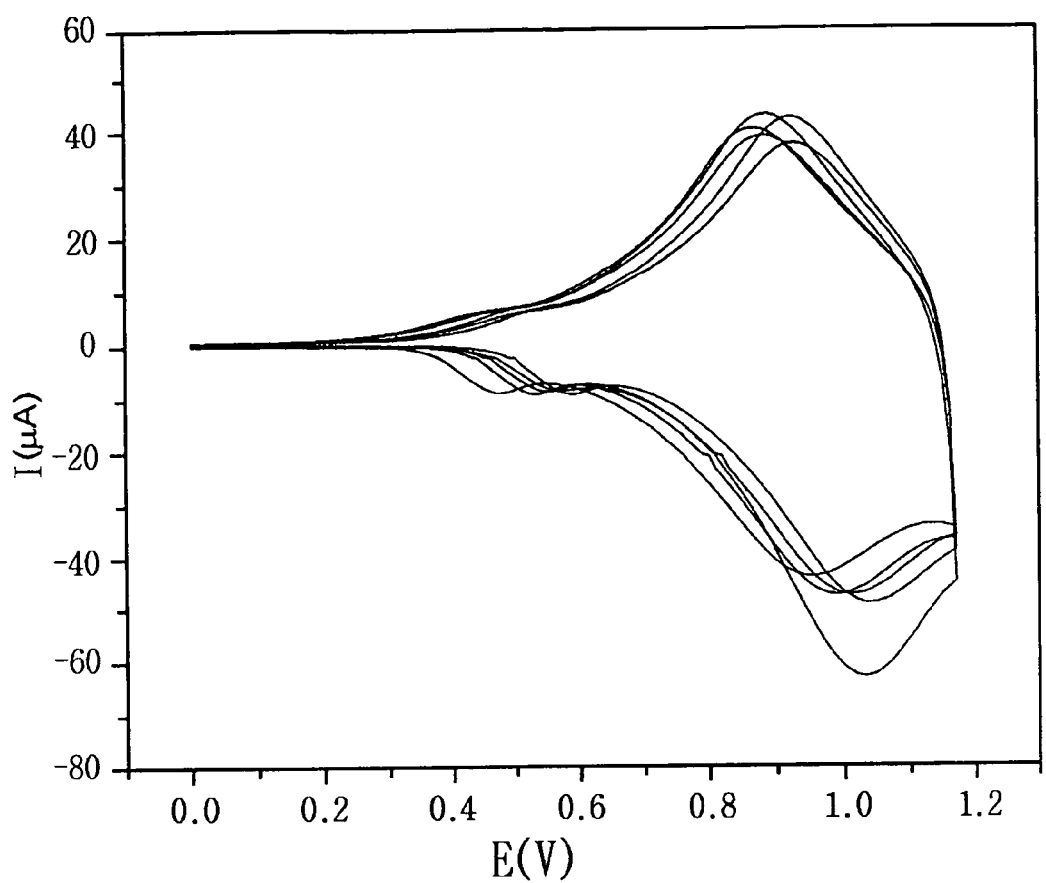
FIG. 5 is a cyclic voltammogram of an electrically conductive polymer layer according to the present invention polymerized by chronopotentiometry.

To measure the reproducibility of the electrically conductive polymer layer of poly(N-hydroxyphthalimidyl 3-thiophenlyl acetate), a cyclic voltammogram was measured five times at a constant scanning rate by applying voltages across the platinum electrode in acetonitrile/TBAHFP. The result is shown in FIG. 5. As shown in FIG. 5, the poly(N-hydroxyphthalimidyl 3-thiophenlyl acetate) layer according to the present invention has a nearly reversible oxidation peak at 1.0V, confirming a high electroactivity of the polymer layer. Apparently, the polymerization reaction over the electrode is highly reproducible.

Figure 6A:
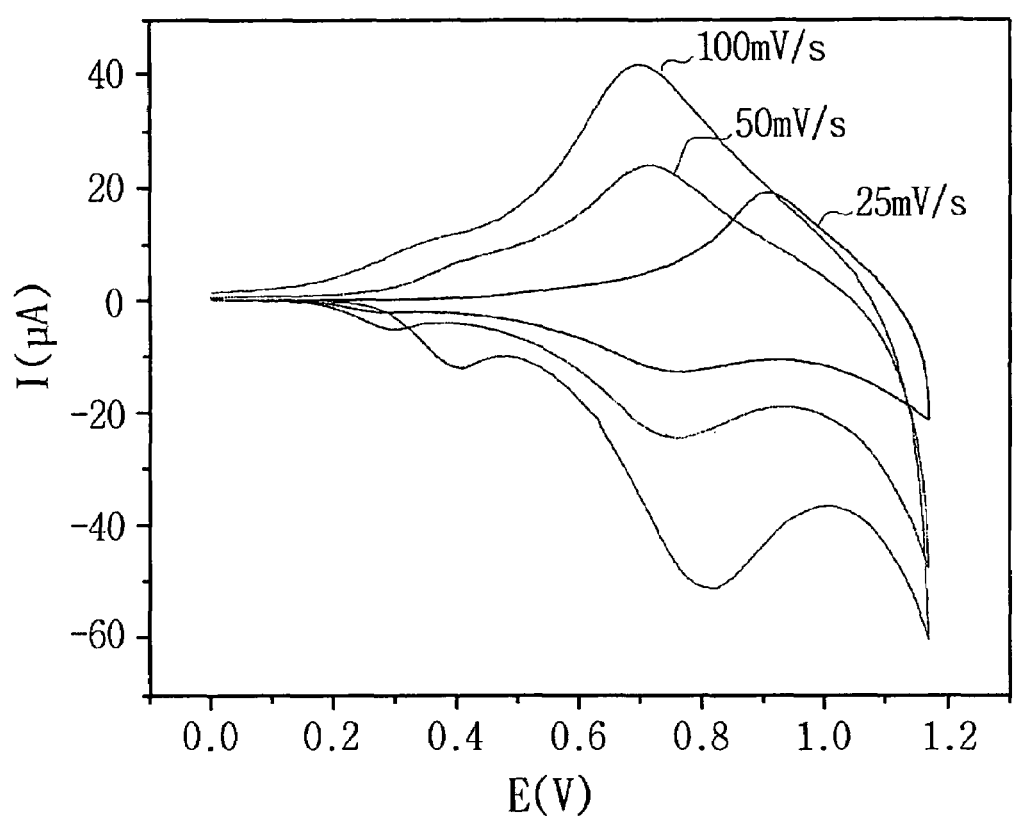
FIG. 6A is a cyclic voltammogram at three different scanning rates for an electrically conductive polymer layer according to the present invention polymerized by chronopotentiometry.
Figure 6B:
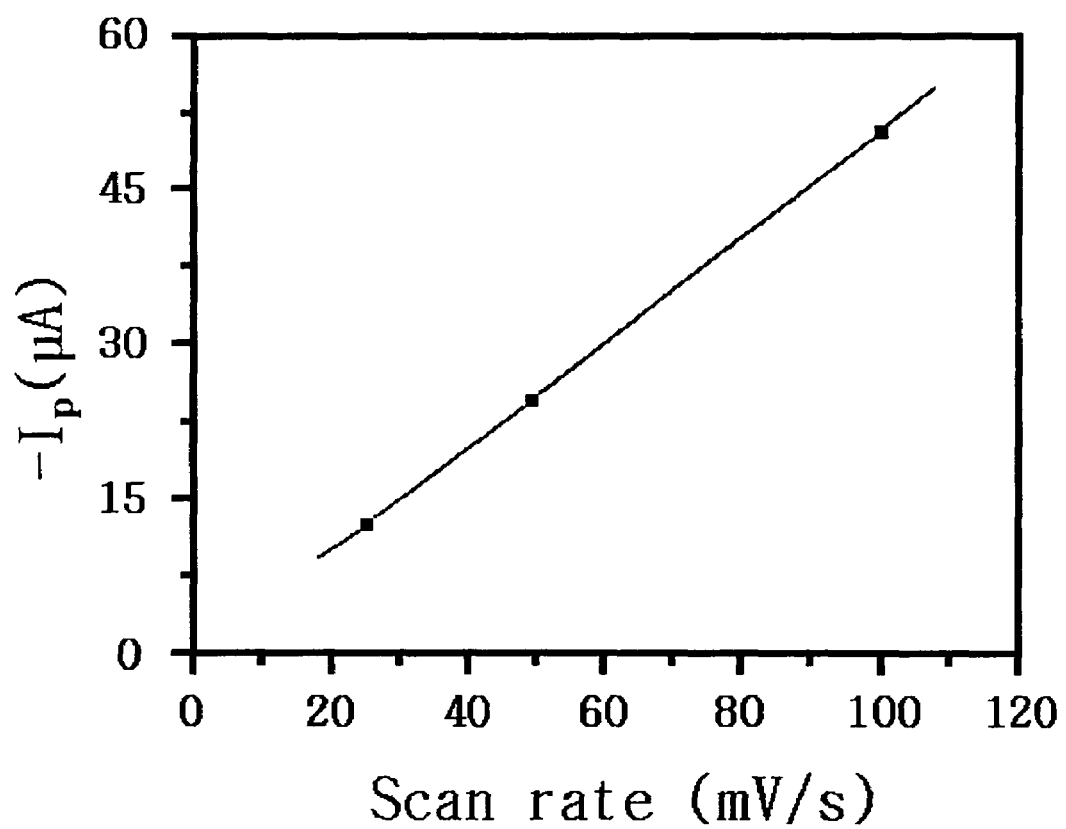
FIG. 6B is a graph of correlation between scanning rate versus and peak current, which was obtained based on the cyclic voltammogram of FIG. 6A.

To measure the electrical conductivity of the poly(N-hydroxyphthalimidyl 3-thiophenlyl acetate) layer, a cyclic voltammogram was measured at three different scanning rates by applying voltages across the platinum electrode. The result is shown in FIG. 6A. FIG. 6B is a graph of correlation between scanning rate versus and peak current, which was obtained based on the cyclic voltammogram of FIG. 6A. As shown in FIG. 6B, the peak current of the polymer layer according to the present invention has a positive linear correlation with the scanning rate, which is indicative of good electrical conductivity of the polymer layer.

EXAMPLE 4

Immobilization of a DNA Probe and Confirmation of its Hybridization with a Target DNA 1. Immobilization of a DNA Probe A DNA probe was immobilized on the electrically conductive polymer layer polymerized in Example 3. 100 µM of probe DNA (5'-NH$_2$-GTTCTTCTCATCATC-3'; SEQUENCE NO. 1) with an amine group at the 5'-terminal was applied to the electrically conductive layer and reacted for about 12 hours. Immobilization of the DNA probe is achieved by the substitution of the 5'-terminal amine group of the DNA probe for a hydroxyphtalimide group of the electrically conductive polymer. Immobilization of a protein probe can be achieved by the substitution of the amine group of lysine residue for the hydroxyphtalimide group of the electrically conductive polymer.

2. Hybridization with a Target DNA

Figure 7:
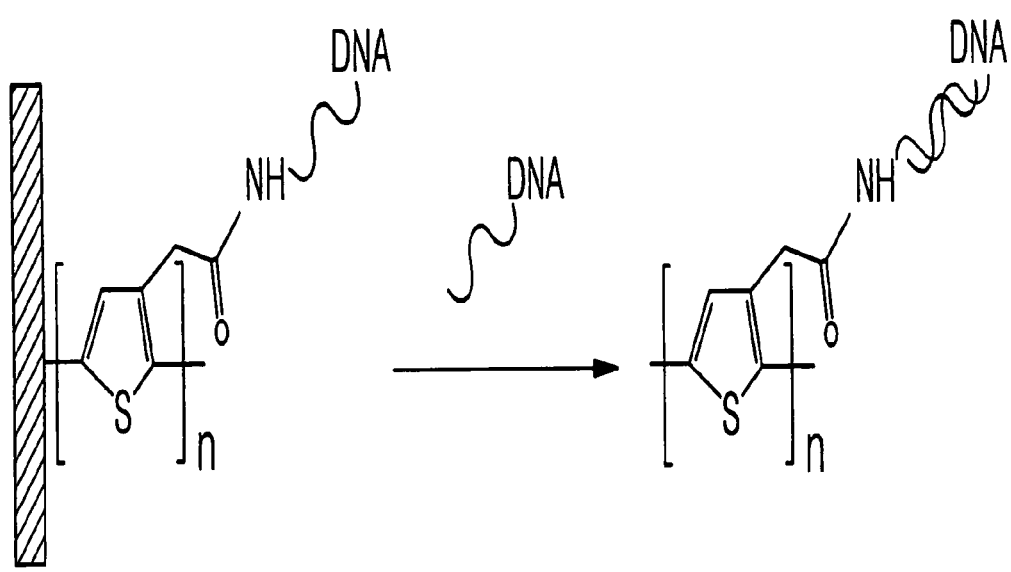
FIG. 7 illustrates the hybridization of an immobilized probe DNA and a complementary target DNA.

100 µM of complementary target DNA (5'-NH$_2$-GATGATGAGAAGAAC-3'; SEQUENCE NO. 2) was applied to the single stranded DNA probe immobilized on the electrically conductive polymer according to the present invention and reacted for hybridization at 40° C. for 3 hours. FIG. 7 illustrates the hybridization of a complementary target DNA to an immobilized probe DNA. As a control group, the single stranded DNA probe was reacted without the complementary target DNA under the same conditions. After the hybridization reaction, a peak current was measured using cyclic potentiometry to confirm hybridization. The result is shown in FIG. 8.

Figure 8:
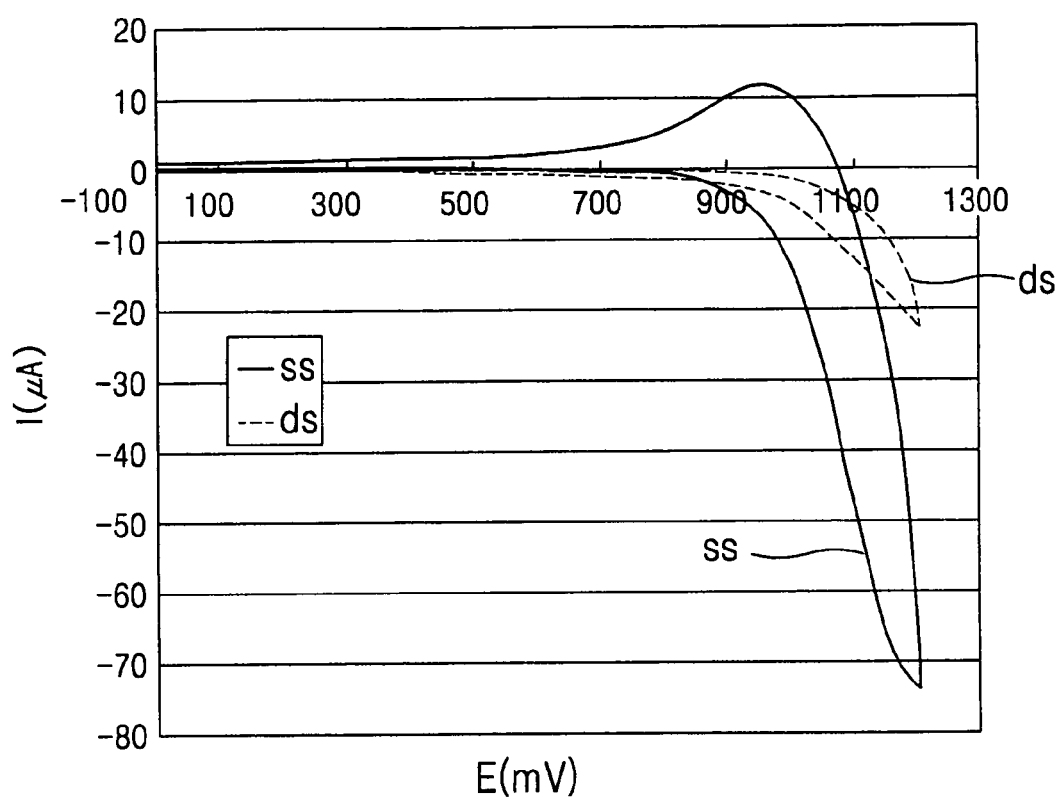
FIG. 8 is a cyclic voltammogram for two spots on an electrode coated with an electrically conductive polymer according to the present invention, one spot for a probe DNA immobilized on the electrode and the other spot for a target DNA hybridized to the probe DNA.

FIG. 8 is a cyclic voltammogram for two spots on an electrode coated with the electrically conductive polymer according to the present invention, one spot for the non-hybridized probe DNA (single stranded; ss) and the other spot for the probe DNA hybridized with the target DNA (double stranded; ds), which was measured to check whether hybridization has taken place or not. As shown in FIG. 8, when DNA hybridization (ds DNA) occurs, a current level at the same voltage greatly decreases. This reduction in current level of the electrically conductive polymer is attributed to a large functional group grafted thereon as a result of the hybridization.

To measure the sensitivity of an electrode coated with the electrically conductive polymer according to the present invention, after hybridization of the probe DNA with different concentrations of the complementary target DNA, a cylic voltammogram was measured. Based on this cyclic voltammogram, a correlation between target DNA concentration and peak current was calculated. The result is shown in FIG. 9.

Figure 9:
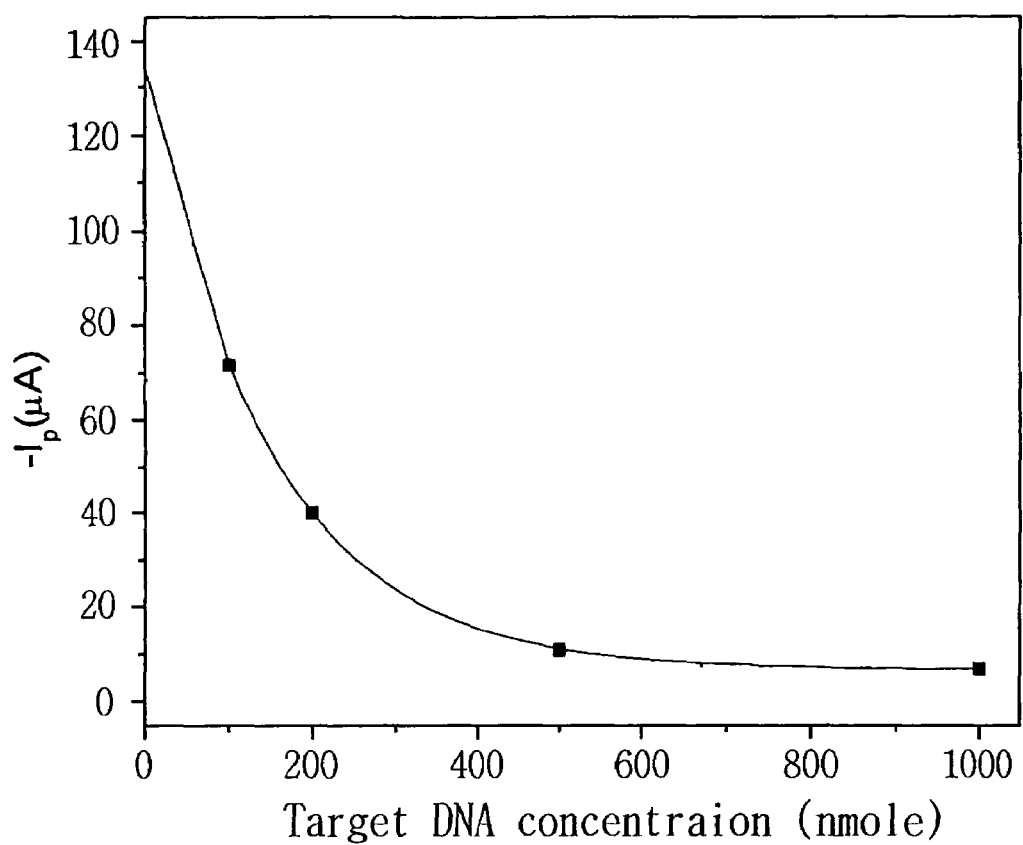
FIG. 9 is a graph of correlation between target DNA concentration and peak current, which is measured from a cyclic voltamogram of target DNA hybridized at different concentrations to probe DNA immobilized on an electrode coated with an electrically conductive polymer according to the present invention.

The sensitivity of the electrode coated with the electrically conductive polymer according to the present invention was calculated from the slope at x=0 of the graph of FIG. 9. The calculated sensitivity of the electrode was 0.62 µA/nmole. This result indicates that a sensor employing the electrode coated with the electrically conductive polymer according to the present invention can detect a target DNA in a sample at a limit of about 1 nmole.

EXAMPLE 4

Hybridization of Target DNA with a Single Base Mismatch

For comparison of the hybridization of a probe DNA with a perfect match target DNA and a single base mismatch target DNA, after the immobilization of DNA probe (5'-NH$_2$-GTTCTTCTCATCATC-3'; SEQUENCE NO. 1) on electrodes coated with the electrically conductive polymer synthesized in Example 3, target DNAs of different sequences were hybridized to the immobilized DNA of the electrodes. The target DNAs used were one perfect match ("PM") DNA, 5'-GATGATGAGAAGAAC-3', (SEQUENCE NO. 2), which perfectly matches the DNA probe, and two single base mismatch DNAs, 5'-GATGATGGGAAGAAC-3' (SEQUENCE NO. 3, "TG") and 5'-GATGATGCGAAGAAC-3' (SEQUENCE NO. 4, "TC"), which have a single non-complementary base to the sequence of the DNA probe. How sensitively and selectively the electrode according to the present invention can detect a single base mismatch was measured from the cyclic voltammograms of the samples. As a control group, a cyclic voltammmogram for the non-hybridized DNA probe was measured. The ratio of peak current of each of the samples to the control group, lp(ds)/lp(ss), was calculated based on the cyclic voltammograms. The results are shown in FIG. 10.

Figure 10:
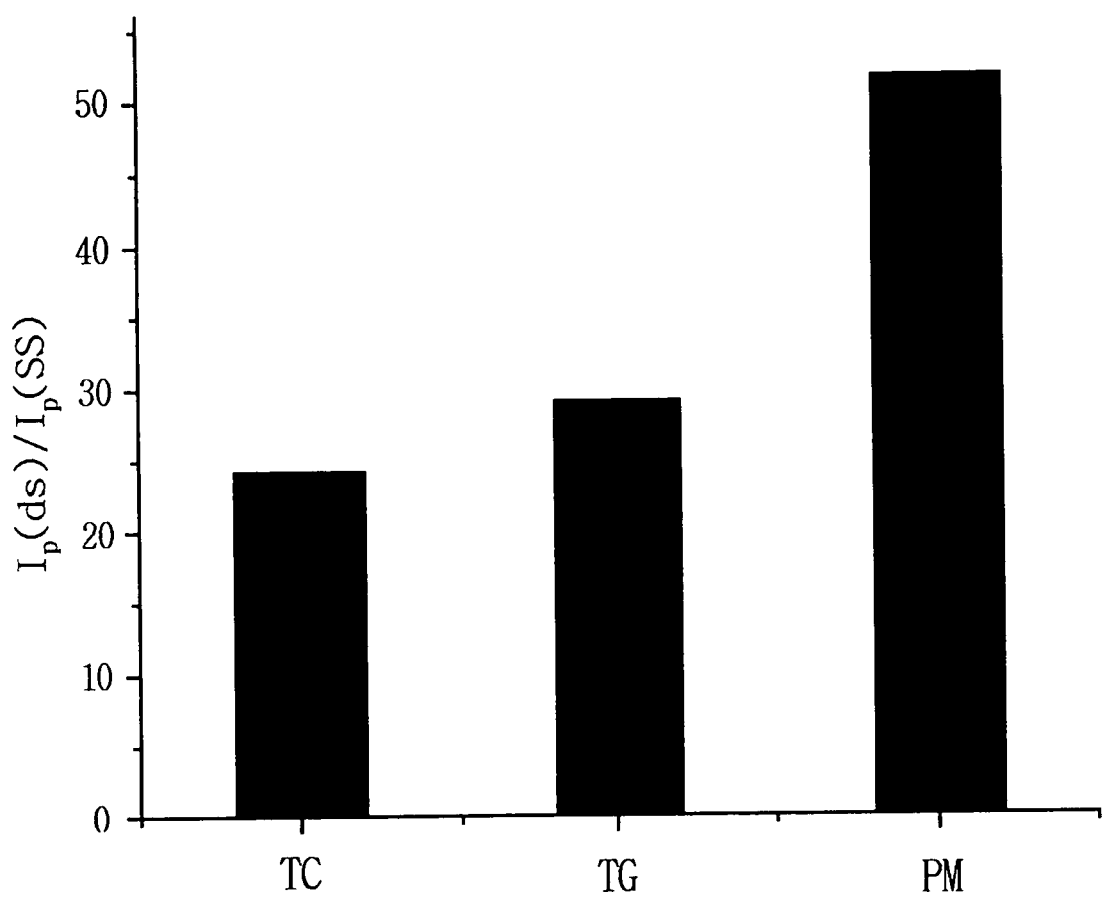
FIG. 10 is a graph showing the difference in peak current between a perfect match target DNA and single base mismatch target DNAs after hybridization to a probe DNA.

As shown in FIG. 10, the ratio of lp(ds)/lp(ss) was 52% for the perfect match target DNA, 29.3% for the single base mismatch TG, and 24.3% for the single base mismatch TC. The ratio of lp(ds)/lp(ss) was much smaller for the single base mismatch target DNAs than for the perfect match target DNA. This result supports that an electrode coated with the electrically conductive polymer according to the present invention can accurately detect a single base mismatch target DNA as well as a perfect match target DNA which are hybridized to a probe DNA immobilized on the electrically conductive polymer.

Monomers according to the present invention can be used to synthesize highly electrically conductive polymers. Electrically conductive polymers according to the present invention can be effectively used in a sensor for detecting the hybridization of a target molecule to a probe. A sensor having an electrode coated with an electrically conductive polymer according to the present invention having a high redox potential according to the present invention can detect the hybridization of a target molecule to a probe, with high selectivity. A target molecule can be rapidly detected with high sensitivity using the method according to the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for detecting a target molecule, comprising:
providing an electrically conductive polymer having a formula (I) on a substrate through electrical polymerization,
wherein the formula (I) is

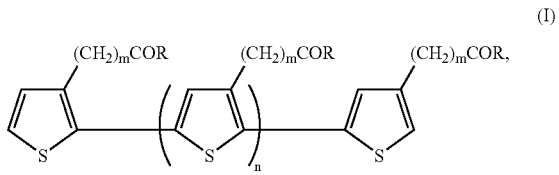
(I)

and where m is 1, 2, or 3; R is a hydroxyphthalimidyl group; and n is zero or an integer;
immobilizing a probe to the surface of the electrically conductive polymer;
contacting a sample containing a target molecule with the probe, to hybridize with the probe; and
detecting the target molecule by measuring a voltage or current variation in the electrically conductive polymer.

2. A method for detecting a target molecule, comprising:
providing an electrically conductive polymer having a formula (II) on a substrate through electrical polymerization,
wherein the formula (II) is

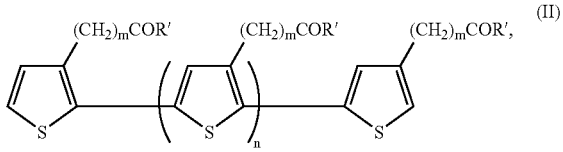
(II)

and where m is 1, 2, or 3; R' is a hydroxyphthalimidyl group or a probe group,
wherein at least one R' is a probe group; and n is zero or an integer;
contacting a sample containing a target molecule with the probe, to hybridize with the probe bonded to the electrically conductive polymer; and
detecting the target molecule by measuring a voltage or current variation in the electrically conductive polymer.

3. The method of claim 1, wherein the conductive substrate comprises a gold electrode or a platinum electrode.

4. The method of claim 1, wherein the probe is selected from the group consisting of a DNA, a RNA, a PNA, an antibody, an antigen, an enzyme, a substrate, and a cofactor.

5. The method of claim 1, wherein the target molecule comprises a nucleic acid or a protein.

6. The method of claim 2, wherein the conductive substrate comprises a gold electrode or a platinum electrode.

7. The method of claim 2, wherein the probe is selected from the group consisting of a DNA, a RNA, a PNA, an antibody, an antigen, an enzyme, a substrate, and a cofactor.

8. The method of claim 2, wherein the target molecule comprises a nucleic acid or a protein.

* * * * *